United States Patent [19]
Reagen et al.

[11] Patent Number: 6,134,004
[45] Date of Patent: *Oct. 17, 2000

[54] OPEN AIR OPTICAL ANALYSIS APPARATUS AND METHOD REGARDING SAME

[75] Inventors: William K. Reagen, Stillwater; Jon R. Erickson, North Branch, both of Minn.; Richard C. Miller, Prescott, Wis.

[73] Assignee: 3M Innovative Properties Company, St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/678,007

[22] Filed: Jul. 10, 1996

[51] Int. Cl.$^7$ ...................................................... G01B 9/02
[52] U.S. Cl. .......................................... 356/346; 356/345
[58] Field of Search ...................................... 356/345, 346

[56] References Cited

U.S. PATENT DOCUMENTS 4,810,092  3/1989  Auth ........................................ 356/346

OTHER PUBLICATIONS

J. Hampel–Stephens et al., "Practical Experiences in Environmental Compliance Auditing for an Air Sampling Program", presented at the 85$^{th}$ Annual Meeting & Exhibition, Air & Waste Management Association, Kansas City, Missouri, Jun. 21–26, 1992 (pp. 1–11).
P. Hanst et al. in *Gas Analysis Manual for Analytical Chemists in Two Volumes: vol. 1, Gas Measurement in the Fundamental Infrared Region*; Infrared Analysis, Inc., pp. 1–77 (undated).
P. Hanst, "94 Catalog—Infrared Analysis, Inc.", pp. 1–24 (1994).
S. Hanst, "Instruction Manual—Long–Path Gas Cell Model #G–3–8–H and #M–3–8–H", Infrared Analysis, Inc., pp. 1–7 (undated).
"FTIR Air Monitoring Systems", brochure of MIDAC Corporation, Costa Mesa, CA, 9 pgs. (undated).
"MIDAC FTIR Air Monitoring System", brochure of MIDAC Corporation, Costa Mesa, CA, 6 pgs (1992).
"Protocol for the Use of Extractive Fourier Transform Infrared (FTIR) Spectrometry for the Analyses of Gaseous Emissions from Stationary Sources", U.S. EPA, *EMTIC Bulletin Board*, pp. 1–33 (Feb. 3, 1995).
A. Wait et al., "Ensuring Environmental Data Quality", presented at the 85$^{th}$ Annual Meeting & Exhibition, Air & Waste Management Association, Kansas City, Missouri, Jun. 21–26, 1992 (pp. 1–11).

*Primary Examiner*—Robert Kim
*Attorney, Agent, or Firm*—Lisa M. Fagan

[57] ABSTRACT

An open air analysis apparatus includes an optical source for providing an optical signal, an interferometer for modulating the optical signal, and an optical signal detector. The apparatus further includes a folded path mirror configuration defining a sample path through which the optical signal passes from the interferometer to the optical signal detector. An enclosure encloses and seals the sample path with the enclosure including at least one removable portion for allowing entry into the sample path of a representative sample of ambient air when the at least one removable portion is removed. The method of gas analysis includes providing an open air spectrometry system defining a sample path. The sample path is enclosed and sealed when the open air spectrometry system is calibrated. The sample path is then opened to allow ambient air therein and analysis of a sample of ambient air in the sample path is initiated. Further, the sample path may be enclosed and sealed after analysis of the sample of ambient air and the open air spectrometry system may be recalibrated to determine the stability of the system during ambient air sample analysis.

31 Claims, 10 Drawing Sheets

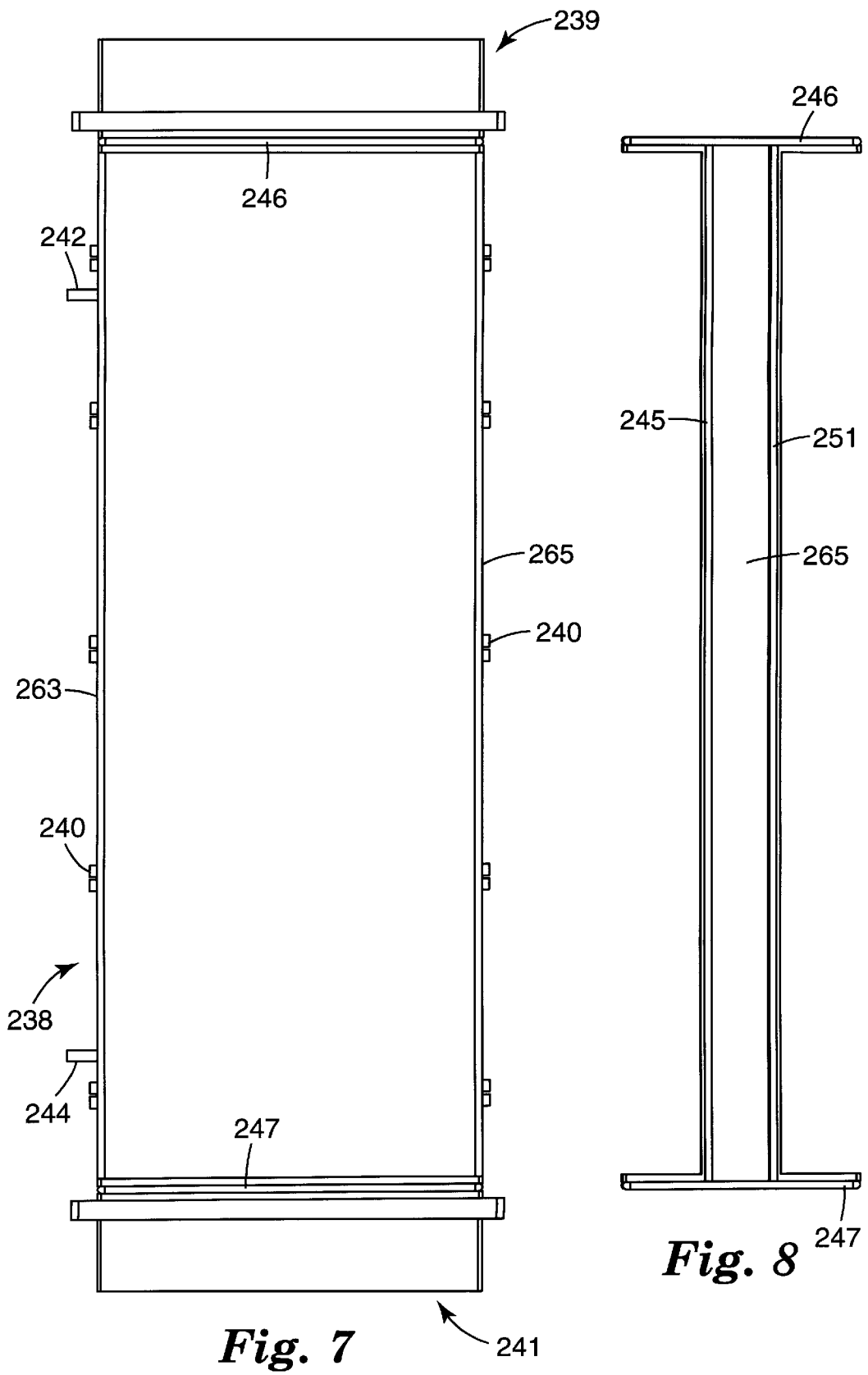

OPEN AIR OPTICAL ANALYSIS APPARATUS AND METHOD REGARDING SAME

FIELD OF THE INVENTION

The present invention relates generally to open air analysis. More particularly, the present invention relates to spectroscopic near real-time open air analysis apparatus and methods.

BACKGROUND OF THE INVENTION

The monitoring of ambient air quality, especially in the workplace, is important not only for complying with legislative permissible levels of various gases or chemical compounds, but also because of the potential health hazards that may be imposed by toxic or flammable gases. As a result, various air quality programs have been utilized for monitoring or analyzing air quality. However, air quality monitoring is only as reliable as the quality of data achieved using currently available air analysis systems, such as Fourier transform infrared (FTIR) gas analysis systems.

Virtually all compounds absorb infrared energy. In FTIR monitoring, infrared energy passes through a sample area, acquiring a characteristic "fingerprint" of the chemicals present due to the unique set of wavelengths they absorb. Currently available FTIR analysis systems for monitoring air quality generally include extractive analysis systems and open air systems. The extractive systems typically consist of a source of mid-infrared radiation, an interferometer, and an enclosed sample cell of known absorption path length, temperature, and pressure. Further, the extractive systems typically include an infrared detector, optical elements for the transfer of infrared radiation between components, and gas flow control and measurement components. Adjunct and integral computer systems and spectroscopic software are used for controlling the FTIR systems, for processing the signals detected by the infrared detector, and for performing both Fourier transforms and quantitative analysis of spectral data. These systems typically monitor many infrared wavelengths simultaneously, and pass on the information detected to the computer system, where it can be transformed into a spectrum. The spectroscopic software analyzes the spectral information. Multi-component analysis of the data can immediately determine which of a certain set of species are present, and how much of each species is present. Further, the spectrum can be analyzed in many cases to determine if any unexpected species were detected; identification of such species can also be made in many cases. The absorption spectrum of pure gases in a mixture of gases are described by a linear absorption theory referred to as Beer's law. Using this law, FTIR systems use the computerized analytical spectroscopic software to quantify compounds by comparing the absorption spectra of known (i.e. reference) gas samples to the absorption spectrum of the sample gas. Such systems normally store the data permanently on a storage media, such as disks, to record the conditions of the site analyzed for use at later times.

Such extractive FTIR systems, available from MIDAC Corp., Costa Mesa, Calif. and others, which use an enclosed sample cell, can be calibrated effectively using known reference gases, i.e. calibration transfer standards, and properly prepared spectral reference data. For example, a calibration transfer standard can be run through the enclosed sample cell resulting in an absorption spectra that, when compared to the standard's known spectra under a different set of conditions pertaining to the spectral reference data, can be utilized to calibrate the FTIR system.

However, unless heated, such extractive FTIR systems utilizing enclosed sample cells cannot always reliably detect various compounds, including many volatile and semi-volatile organic compounds at low concentration levels, such as 10 ppm and below. The sampling and handling utilized with extractive FTIR systems, such as when air is collected as a grab sample at a site to be monitored and then transported to an extractive analysis system, leads to less than desirable quality for the data resulting from the extractive analysis then performed. For example, the grab sample may not be a homogenous representative sample of ambient air at the site being assessed. Further, at low concentrations, both the enclosed sample cell utilized to perform the analysis, and the container utilized for transport of the air sample, can significantly affect the concentration levels of various compounds within such structures. For example, many compounds will react with the wall structures or may stick to wall structures of the enclosed sample cell or transport container such that when analysis is performed, accurate concentration levels are not in the sample path of the system and therefore, not effectively measured. In addition, the time required to obtain results from such a process using a grab sample and off-site analysis is relatively long.

The open air analysis systems available, such as FTIR open air analysis systems, typically include elements like those of the extractive systems but do not utilize an enclosed sample cell. Such open air analysis systems are currently available from MIDAC Corporation, Costa Mesa, Calif. and others. These open air analysis systems, for example, are said to have versatility in that they are able to monitor multiple gas species simultaneously over large sample areas, can provide results in very little time, and are said to be portable and capable of running on battery power in remote locations. However, such systems utilize components that are unconnected physically and located at a substantial distance from one another. For example, such systems may be utilized for fence line monitoring where the interferometer, source, and detector are all located on the ground a substantial distance from reflective elements of the system, i.e. about the perimeter of a particular site. However, because of the large distances between components used to obtain an adequate pathlength for the system, such open air systems cannot be effectively field calibrated, i.e. recording of calibration transfer standard (CTS) spectra in the field. An enclosed sample cell cannot be utilized to encompass such a large sample volume between the components of such an open air system. Therefore, there is no enclosed sample cell into which a calibration transfer standard can be introduced. In addition, the large linear distance between components allows the possibility that the effective sample is not at uniform or nearly uniform temperature. It is clear from these considerations, that the quality and validity of such data collected utilizing such open air monitoring systems is questionable.

For the above reasons and the reasons that will become apparent from the description below, improvements to open air analysis systems and methods for performing such open air analysis are needed. For example, there is a need for open air analysis systems and methods that can perform near real-time on site analysis and have the capability to demonstrate instrument calibration using gas flows of, for example, calibration transfer standards.

SUMMARY OF THE INVENTION

An open air analysis apparatus of the present invention includes an optical source for providing an optical signal, an interferometer for modulating the optical signal, and an optical signal detector. A folded path mirror configuration of the apparatus defines a sample path through which the optical signal passes from the interferometer to the optical signal detector. An enclosure for enclosing and sealing the sample path includes at least one removable portion for allowing entry into the sample path of a representative sample of ambient air when the at least one removable portion is removed.

In various embodiments, the folded path mirror configuration may be a White cell folded path mirror configuration and/or the enclosure may include a sample inlet port and a sample outlet port.

In yet another embodiment of the apparatus, the enclosure may include at least a first and second removable portion. Yet further, the enclosure may include a frame structure having a first and second end for supporting the folded path mirror configuration therebetween. The first and second removable portions are positioned within the frame structure about the sample path such that when the first and second removable portions are removed, air moves into the sample path from substantially all directions between the first and second ends.

In other embodiments of the apparatus, an air movement device may be utilized for providing the representative sample of ambient air to the sample path when the at least one removable portion is removed, the apparatus may be configured as a movable standalone open air analysis apparatus powered by a battery source, and the movable standalone analysis apparatus may include a processing device for receiving data signals from the optical signal detector.

A device for an optical analysis system in accordance with the present invention includes a folded path mirror configuration defining a sample path through which an optical signal is passed and an enclosure for enclosing and sealing the sample path. The enclosure includes at least one removable portion for allowing entry into the sample path of a representative sample of ambient air when the at least one removable portion is removed.

An open air analysis system in accordance with the present invention includes an open air spectrometry apparatus including a folded path mirror configuration defining a sample path. The open air spectrometry apparatus has a calibrated state and an uncalibrated state. An enclosure encloses and seals the sample path. The enclosure includes at least one removable portion to provide the sample path with a representative sample of ambient air when the at least one removable portion is removed while maintaining the calibrated state.

In one embodiment of the system, the spectrometry apparatus may include an optical source for providing an optical signal, an interferometer for modulating the optical signal, and an optical signal detector. Further, the folded path mirror configuration defines the sample path through which the optical signal passes from the interferometer to the optical signal detector. Yet further, in another embodiment, the spectrometry apparatus is a Fourier transform infrared spectrometry apparatus and the optical source is an infrared source.

A method of gas analysis of the present invention includes providing an open air spectrometry system defining a sample path. The sample path is enclosed and sealed while the open air spectrometry system is calibrated. The sample path is opened to allow ambient air therein and analysis of a sample of ambient air in the sample path is initiated.

In one embodiment of the method, the sample path is again enclosed and sealed after analysis of the sample of ambient air. The open air spectrometry system is then recalibrated to determine the stability of the system during ambient air sample analysis.

In another embodiment of the method, the method further includes the step of locating the open air spectrometry system in a first environment. The open air spectrometry system is then moved to a second environment and the enclosing, calibrating, opening, and initiating steps are repeated.

BRIEF DESCRIPTION OF THE DRAWINGS

FIG. 2b is an illustration of part of the mirror configuration of FIG. 2a;

FIG. 2c is an alternative illustration of part of the mirror configuration of FIG. 2a;

FIG. 2d is an alternative illustration of part of the mirror configuration of FIG. 2a;

FIG. 7 is a front view of an inner frame structure of the local open-path infrared spectrometry system shown in FIG. 3 upon which the removable cover is mounted;

FIG. 8 is a side view of a portion of the frame structure shown in FIG. 7;

DETAILED DESCRIPTION OF THE EMBODIMENTS

Figure 1:
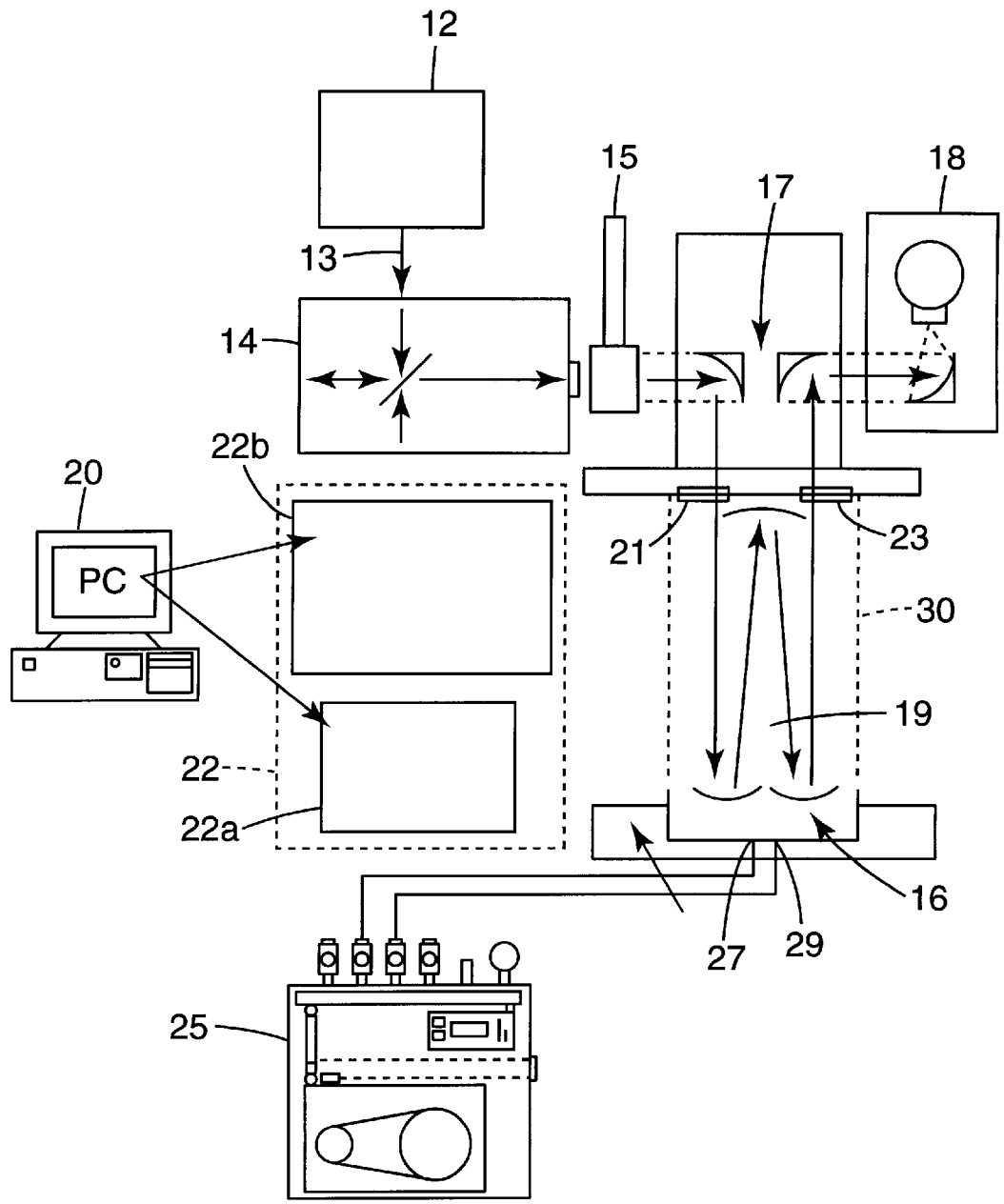
FIG. 1 is a block diagram of a local open-path infrared spectrometry system in accordance with the present invention.

The long term exposure of workers to low levels of hazardous substances in the work place can have serious health consequences. Measurements of gaseous agents for compliance demonstrations and remediation efforts are typically achieved with sample collection devices and subsequent laboratory analyses, i.e. some extractive analysis systems. However, on-site infrared absorption spectrometry provides more useful and cost effective measurements of low-level gaseous pollutants than the typical "grab" sample technique (previously described in the Background of the Invention). The mobile local open-path infrared spectrometry system 10, as shown in FIG. 1, is capable of performing such on-site infrared absorption spectrometry producing high quality and highly reliable data.

The mobile local open-path infrared spectrometry system 10 possesses the advantages of conventional open-path or open air infrared absorption spectrometry systems as described in the Background of the Invention, such as the ability to obtain near real-time monitoring of multiple gas species simultaneously over large sample areas, and the portability and capability of running on battery power in remote locations. Yet, the spectrometry system 10 can be calibrated in the same way as extractive analysis systems. This combination of advantages is achieved through the use of a folded path optical mirror configuration 16, such as a White cell mirror configuration, which yields a large absorption path length. Further, the spectrometry system 10, in order to provide the calibration advantage, includes a removable cover 30, shown by the dashed line of FIG. 1, which completely encloses and seals the sample volume through which the light beam is reflected by the folded path mirror configuration 16, allowing the introduction of calibration standard gases immediately before the analysis of air samples for calibration of the system. After calibration, the cover 30 can then be removed to provide a homogenous, localized, representative sample of ambient air into the sample path for analysis. This is unlike the standard open air measurement devices described in the Background of the Invention, in which the physical distance of the sample path is orders of magnitude larger than the sample path in accordance with the present invention, cannot be isolated for calibration, is not necessarily homogenous, and is not localized.

The local open-path infrared spectrometry system 10 employs Fourier transform (FT) spectrometry techniques, which provide extremely low signal-to-noise ratios, response times on the order of seconds to minutes, and large infrared bandwidth. Extractive FTIR systems have been proven extremely effective in measurements of molecular concentrations in complex gas mixtures, and FTIR methodologies for compliance air emission testing have been substantially defined, such as in the protocol, U.S. EPA, "Protocol for the Use of Extractive Fourier Transform Infrared (FTIR) Spectrometry for the Analysis of Gaseous Emissions from Stationary Sources," *EMTIC Bulletin Board* (Feb. 3, 1995). Such extensive quality assurance and control procedures developed for extractive FTIR methods are directly applicable to the local open-path infrared spectrometry system 10 as described herein and this protocol is incorporated herein in its entirety by reference. This protocol is capable of being utilized because the spectrometry system 10 can be calibrated in the same manner as an extractive system.

The present invention shall now be described in further detail with reference to FIGS. 1 and 2. The mobile local open-path infrared spectrometry system 10, as shown generally in the block diagram of FIG. 1, includes an infrared source 12 generating a light beam 13 in the infrared region, i.e. 0.78 to 800 micron wavelength of the electromagnetic spectrum, particularly in the mid-infrared region of approximately 4.0 to 50 microns. The light beam 13 is modulated utilizing an interferometer 14 as is known to one skilled in the art. For example, the interferometer 14 divides the light beam 13 into two or more paths using a beam splitter (i.e. such as a ZnSe beam splitter), generates an optical path difference between the beams, and recombines them in order to produce repetitive interference maxima and minima as the optical path difference is varied. The modulated light beam from the interferometer 14 is transferred to the folded path optical mirror configuration 16 by means of transfer optics 17 and laser alignment device 15. The laser alignment device 15 is for the precise determination of the position of the mirrors. The modulated light beam is provided to the sample path 19, i.e. sample volume, defined by the folded path mirror configuration 16 through an optical window 21. The modulated light beam passes multiple times in the mirror configuration 16 prior to exiting the sample path 19 through an optical window 23 for transfer by way of transfer optics 17 to an infrared detector, i.e. photo detector 18. The infrared detector 18 then provides data signals as known to one skilled in the art to associated computer equipment 20. The optical windows may be any standard infrared window, e.g. NaCl windows.

The associated computer equipment 20 includes associated spectral data collection and spectroscopic analysis software and spectral reference data 22 for quantifying compounds by comparing absorption spectral data of known (i.e. reference) gas samples to the absorption spectrum of the air sample in the sample path 19, for example, a homogenous, localized, representative sample of ambient air in accordance with the present invention. Such spectroscopic analysis software 22 may include standard mathematical techniques used for such comparisons, such as classical least squares, inverse least squares, cross-correlation, factor analysis, partial least squares, and any other mathematical techniques used in conventional spectrometry systems for gas or air analysis.

Figure 2A:
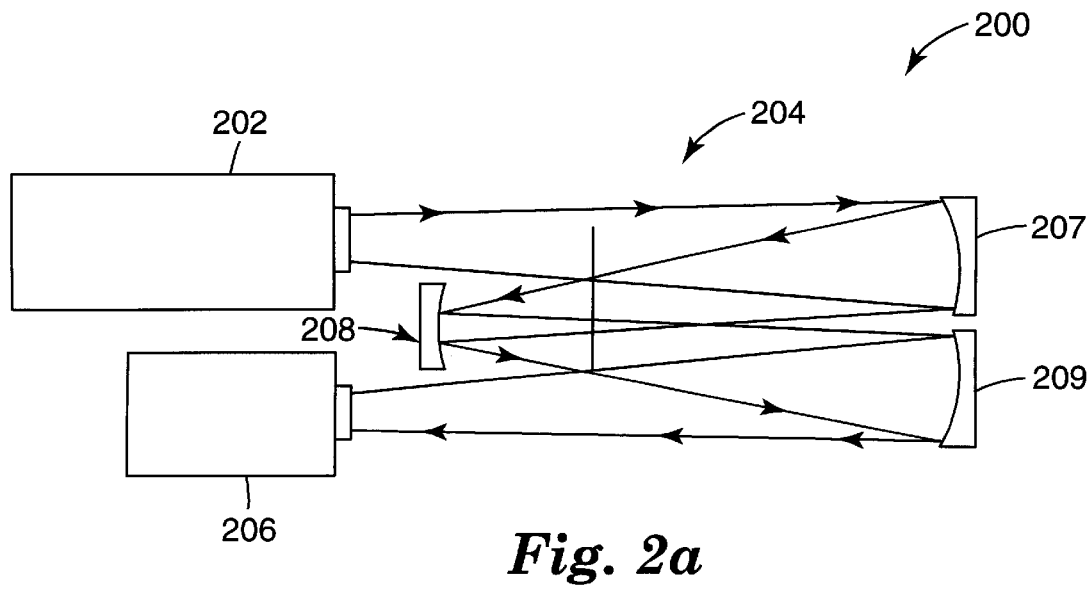
FIG. 2a is an illustration of a prior art White cell folded path optical mirror configuration.

The above elements, in general, are the typical components of extractive gas analysis systems, readily known to those skilled in the art. However, local open-path spectrometry system 10 further includes removable cover 30. For example, such elements other than the removable cover 30 may be part of a conventional White cell as illustrated in FIG. 2a. The typical White cell 200 includes an interferometer source 202 for providing a modulated laser beam to folded path optical mirror configuration 204 which transfers the modulated light beam to a detection system 206 thereof. The folded path optical mirror configuration 204 generally includes three mirrors, including a field mirror 208 and two objective mirrors 207 and 209.

Figure 2B:
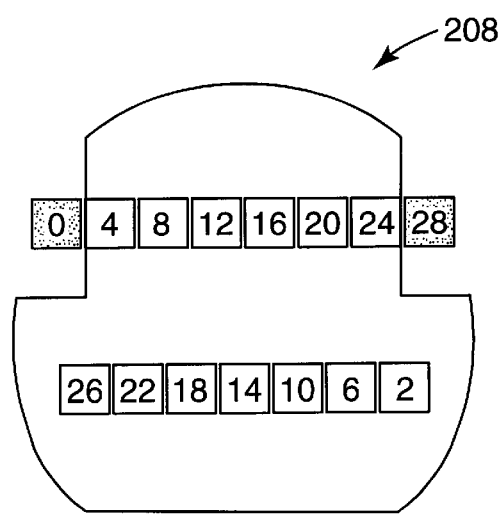

The field mirror 208 of a typical White cell mirror configuration is further shown in FIG. 2b. Reference shall be made with regard to the field mirror 208 to describe the operation of the cell utilizing the folded path optical mirror configuration 204. In operation of the White cell, the light from the interferometer source 202 is provided into the cell and through at least four passes. The light beam from the source 202 is initially focused into a real image in the entrance aperture of the cell. In FIG. 2b, this entrance aperture is designated the zero image. After passing through the zero image, the beam diverges and is collected by objective mirror 207. The objective mirror 207 is a spherical mirror situated two focal lengths from the image so that it refocuses the image, inverted, on the lower part of the opposite field mirror 208. The first image is marked "2" for two passes. The field mirror 208 is aimed so that the reflected diverging beam falls entirely on the second objective mirror 209. This is then aimed to form another image, marked "4" (FIG. 2b) about the central line of the field mirror 208 along side the zero image. If this image falls symmetrically opposite the first image (marked "2"), the beam will be returned to the first objective mirror 207 at the required small angle with the input beam, so that all the energy is again collected and returned and there will be at least four more passes through the folded path optical mirror configuration 204.

Figure 2C:
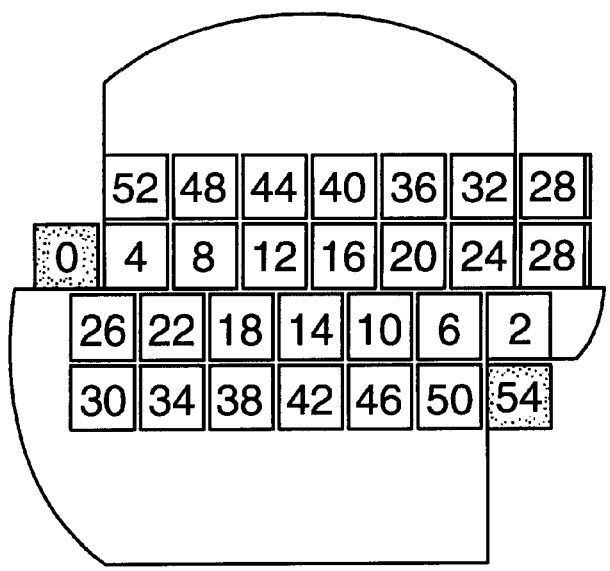
Figure 2D:
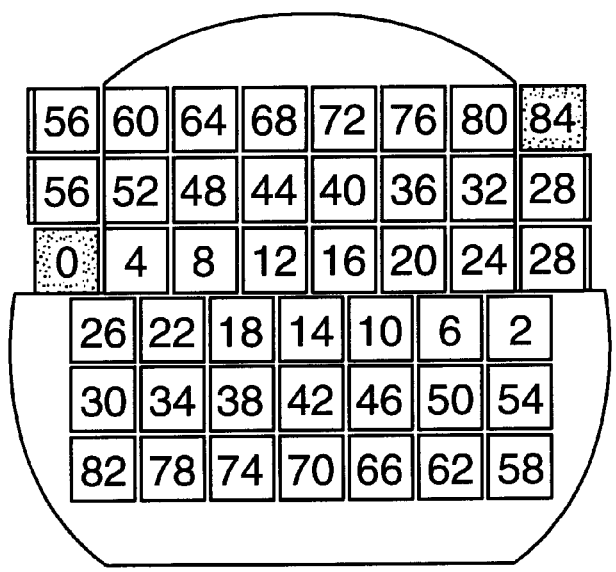

As shown in FIG. 2c, modifications to the field mirror utilizing a retroreflecting pair of mirrors 28 at the normal exit port increases the amount of available mirror surface at the field mirror side of the cell. This allows the use of a more collimated light, thus increasing the energy throughput without enlarging the main collecting mirrors. Two additional rows of images double the number of passes by means of the retroreflective mirrors. This increased sample path length in turn provides lower detection limits for the gases in the sample path. Further, as shown in FIG. 2d, a second retroreflecting pair of mirrors 56 on the input side of the field mirror is added to create six rows of images. Again, this increases the sample path length and, in general, lowers the detection limits.

As would be readily apparent to one skilled in the art and as shown above, various alternative mirror configurations are possible along with various components that form the spectroscopic portions of the system 10. The present invention utilizing removable cover 30 and a folded path mirror configuration 16 that defines the sample path 19 of the system 10, can be utilized with many different folded path mirror configurations and spectroscopic components. For example, the present invention including the removable cover 30, can be used with any of the White cell mirror configurations 204 shown in FIG. 2 and any other folded path mirror configurations as described in the publication "Gas Analysis Manual for Analytical Chemists in Two Volumes—Volume 1—Gas Measurement in the Fundamental Infrared Region", by Philip L. Hanst and Steven T. Hanst and in the 1994 Catalog "Infrared Analysis, Inc.— Specialists in the Measurement of Gases", each of which is entirely incorporated herein by reference. Such mirror configurations are available from Infrared Analysis, Inc., Irvine, Calif. Other mirror configurations incorporating folded optical paths are applicable (e.g. a Wilkes cell mirror configuration) and any other folded path mirror configuration of similar nature known to those skilled in the art may also be utilized in conjunction with the present invention.

Suitable multi-pass mirror configuration 16 requires only that the optics provide a long absorption path length to achieve low detection limits. The optical path length should be in the range of about 1 m to about 200 m, preferably about 80 m to about 120 m.

Further, any suitable spectrometry system and components thereof having a folded path mirror configuration that provides an optical path of suitable length can be utilized in conjunction with the present invention. For example, any suitable spectroscopic software and computer system that performs the system control, data processing of detected information, and quantitative analysis of spectral data as required by the user may be utilized. Further, any optical source that provides a desired light beam 13, any interferometer 14 that provides suitable modulation of the light beam as desired by the user, any optical detector 18 that is capable of detecting the light beam after it has been reflected multiple times in the sample path by the mirror configuration 16, may be utilized as would be apparent to one skilled in the art.

In accordance with the present invention, the sample path 19 which is defined by the volume through which the modulated light beam passes in the folded path mirror configuration 16 is enclosed by the removable cover 30. The removable cover 30 as shown generally by the dashed line of FIG. 1, and structure associated therewith, as will become apparent from the detail description below, includes structure for the connection of a gas control flow and measurement components 25 for use in calibrating the system 10 with standard calibration gases, i.e. calibration transfer standards (e.g. ethylene 1 ppmv). Such gas control flow and measurement components 25 can include components such as a vacuum pump, mass flow controllers, compressed gases, rotometers, vacuum/pressure gauges, sample lines, and feedings and safety valves as is known to those skilled in the art and which are commonly used in extractive analysis systems. The gas flow control and measurement components 25 are fluidly coupled to the sample path with input and output valves 27, 29. The description below with respect to one particular embodiment of the present invention, shows the input and output valves on structure that remains when the removable cover 30 is removed from the sample path. However, as would be known to one skilled in the art, such valves could be provided in other manners, such as on the removable cover 30 itself.

The method in accordance with the present invention utilizing the local open-path infrared spectrometry system 10 involves locating the movable spectrometry system 10 to a facility or location at which air analysis is to be performed. The system 10 is then calibrated. After the system 10 is calibrated, the removable cover 30 is removed and analysis of a homogenous representative sample of ambient air in the sample path is initiated. After the near real-time analysis of the air sample is performed, the removable cover 30 of the system is repositioned to enclose and seal the sample path and the system is recalibrated to determine the stability of the system. The movable system can then be moved to another location and the steps repeated. Alternatively, the system can be moved to numerous locations, samples taken at such locations, and then recalibrated.

The field calibration of the system 10 is typically performed in the following manner. However, one skilled in the art will recognize that various deviations from this particular calibration process are possible while still achieving the calibration objective in accordance with present invention. After the system 10 is located at the site to be monitored, the system 10 with its removable cover 30 in place is purged with a background gas, for example, dry nitrogen, using the gas sample manifold 25 and the inlet and outlet valves 27 and 29. Other high purity gases may also be utilized to establish a background spectrum, for example, dry air, humidified nitrogen, and humidified air. A single beam spectrum or interferogram for the background gas in the sample path 19 is collected to use as background spectrum for subsequent calibration and data collection. Single beam spectrum in an FTIR system is the Fourier transformed interferogram that represents the detector response versus wavelength (i.e. infrared frequency). The interferogram is the optical signal detector response provided to the computer system 20 and is a measurement based on the optical path difference of the modulated light beam passed through the sample path 19.

Likewise, a water reference spectrum is collected in the following manner during calibration. First, with the removable cover 30 removed, an air background single beam spectrum of a representative sample of air at the location being analyzed is collected. Second, with the removable cover 30 put back in place, the air background spectrum collected is operated in an active absorbance align mode. A high purity gas (the same gas used in establishing the background spectrum), such as nitrogen, is humidified, such as by bubbling the gas through a water impinger or using any other technique for humidifying a gas as known to one skilled in the art. The humidified high purity gas is then flushed through the enclosed sample path 19 until water absorbance levels closely match the ambient air levels as previously recorded. A single beam spectrum of the humidified high purity gas is then collected. The single beam spectrum of humidified gas is then converted to an absorbance spectrum using the high purity dry gas background spectrum previously collected. The absorbance spectrum is saved as a water reference spectrum and used for spectral subtraction of sample data. Spectral subtraction is performed to remove spectral interferences from water in the ambient air.

Optical pathlength calibration for the system 10 is then determined quantitatively by using a calibration transfer standard (CTS). The CTS is a gas standard of a compound used to achieve and/or demonstrate suitable quantitative agreement between sample spectra and the reference spectra, i.e. reference spectra being the absorption spectra of gases with known chemical compositions recorded at a known absorption pathlength which are used in the quantitative analysis of the sample spectra. In performing optical path length calibration, the enclosed sample path is flushed with the CTS. A single beam spectrum of the CTS is collected and the single beam spectrum of CTFS is converted to an absorbance spectrum using the high purity dry gas background spectrum previously collected. The CTS absorbance spectrum is quantified using a CTS reference spectrum to determine the optical path length. Various CTSs are available and suitable for calibration, such as ethylene, carbon monoxide, and methane, readily available from commercial gas suppliers, e.g. Scott Specialty Gases.

After the optical path length calibration is performed, field calibration is completed and the removable cover 30 is removed to sample ambient air. With the removable cover 30 removed from sample path 19 or in other words, the sample path being opened to the ambient air, a homogenous representative sample of ambient air is present in the sample path 19. A single beam spectrum of the ambient air sample is collected. The single beam air spectrum is then converted to absorbance spectra using the background spectrum previously collected. The sampled absorbance spectra of the ambient air is then quantified using a known reference spectrum to determine levels of the gas or gases present in the air at the site being monitored which correspond to reference spectrum for such gas or gases at concentrations of parts per million by volume (ppmv).

At the end of the ambient air sampling, the optical path length is once again determined quantitatively by using the CTS with the removable cover 16 replaced on the spectrometry system 10. Then, the enclosed infrared spectrometry system 10 is flushed with the CTS and a single beam spectrum of the CTS is collected. The single beam spectrum of CTS is converted to an absorbance spectrum using the background spectrum previously collected. The CTS absorbance spectrum is then quantified using the CTS absorbance spectrum generated during initial calibration to determine the instrument and optical path length stability throughout the air sample analysis process, from initiation to completion.

The spectrometry system 10 can be sequentially moved to various locations at a particular site and air sample data can be collected throughout the particular site at the selected sampling areas. The system 10 can be thought of as a calibrated "on-line" local open path infrared spectrometry system 10 that provides near real-time data for the area being monitored. It should be readily apparent to one skilled in the art that the mobile system 10, after initial calibration, can be calibrated or recalibrated at any time during the monitoring process. For example, calibration may be performed each time the system is moved or after several selected sample areas have been analyzed. Further, for example, recalibration need not be performed after each selected sample area has been analyzed, but one or more times throughout the monitoring of a particular site or at the end of monitoring a particular site through sampling of air at a number of different places.

One particular embodiment of the movable local open-path infrared spectrometry system 10 utilized in the method for air analysis is shown in the FIGS. 3–9. It will be readily apparent to one skilled in the art that the embodiment described herein of the movable local open-path infrared spectrometry system 10 may be configured in a number of different manners as will become apparent from the description below. However, the different configurations which may be suitable for the local infrared open-path spectrometry system 10 are required to provide a folded path optical mirror configuration defining a sample path and have a removable cover about the sample path. With the removable cover in place, calibration of the system 10 may be performed. With the cover removed, a homogenous representative sample of ambient air is allowed into the sample path for analysis.

Figure 3:
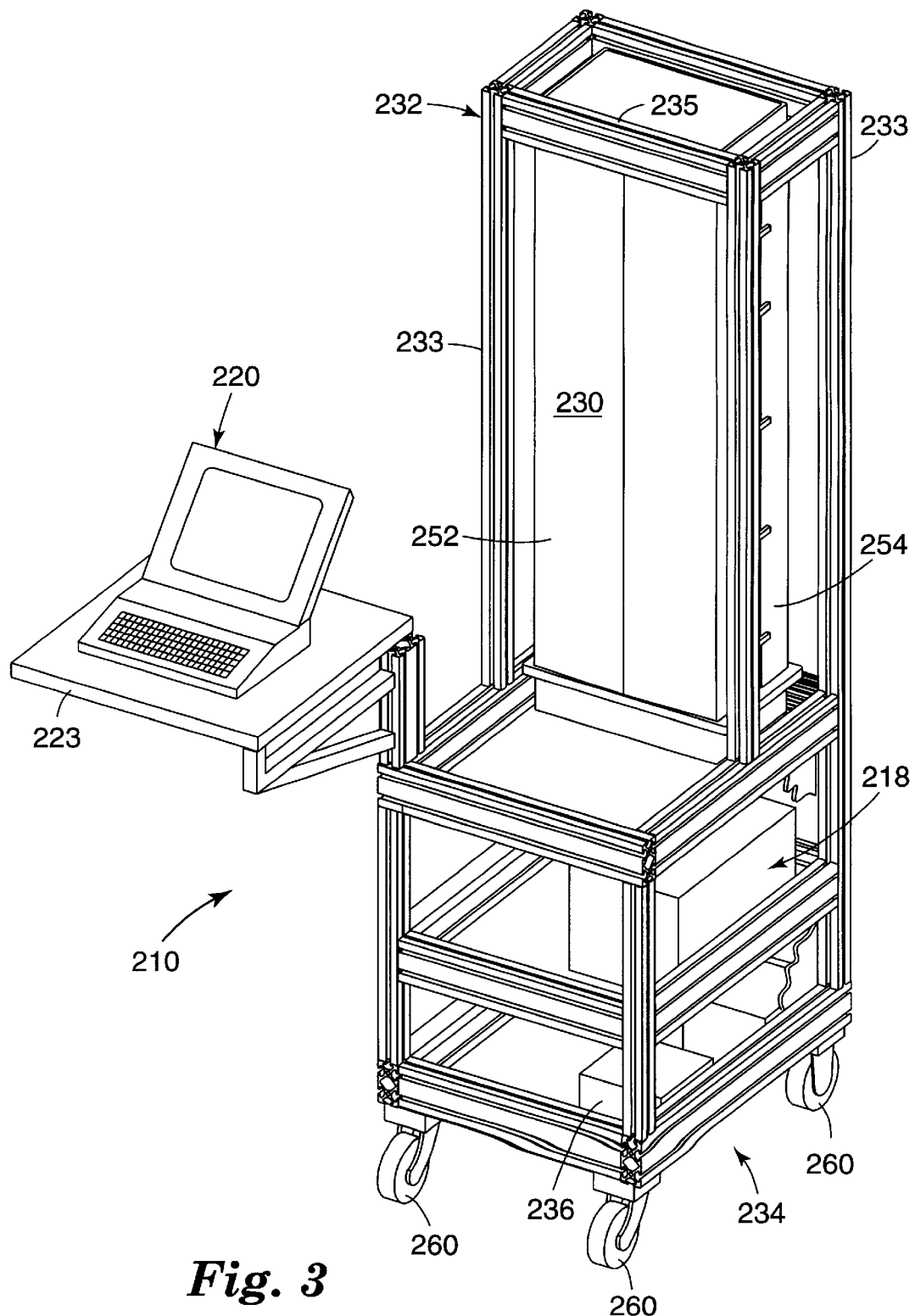
FIG. 3 is a perspective view of one embodiment of a local open-path infrared spectrometry system generally shown in FIG. 1 with the removable cover in place for enclosing and sealing a sample path of the system in accordance with the present invention.
Figure 4:
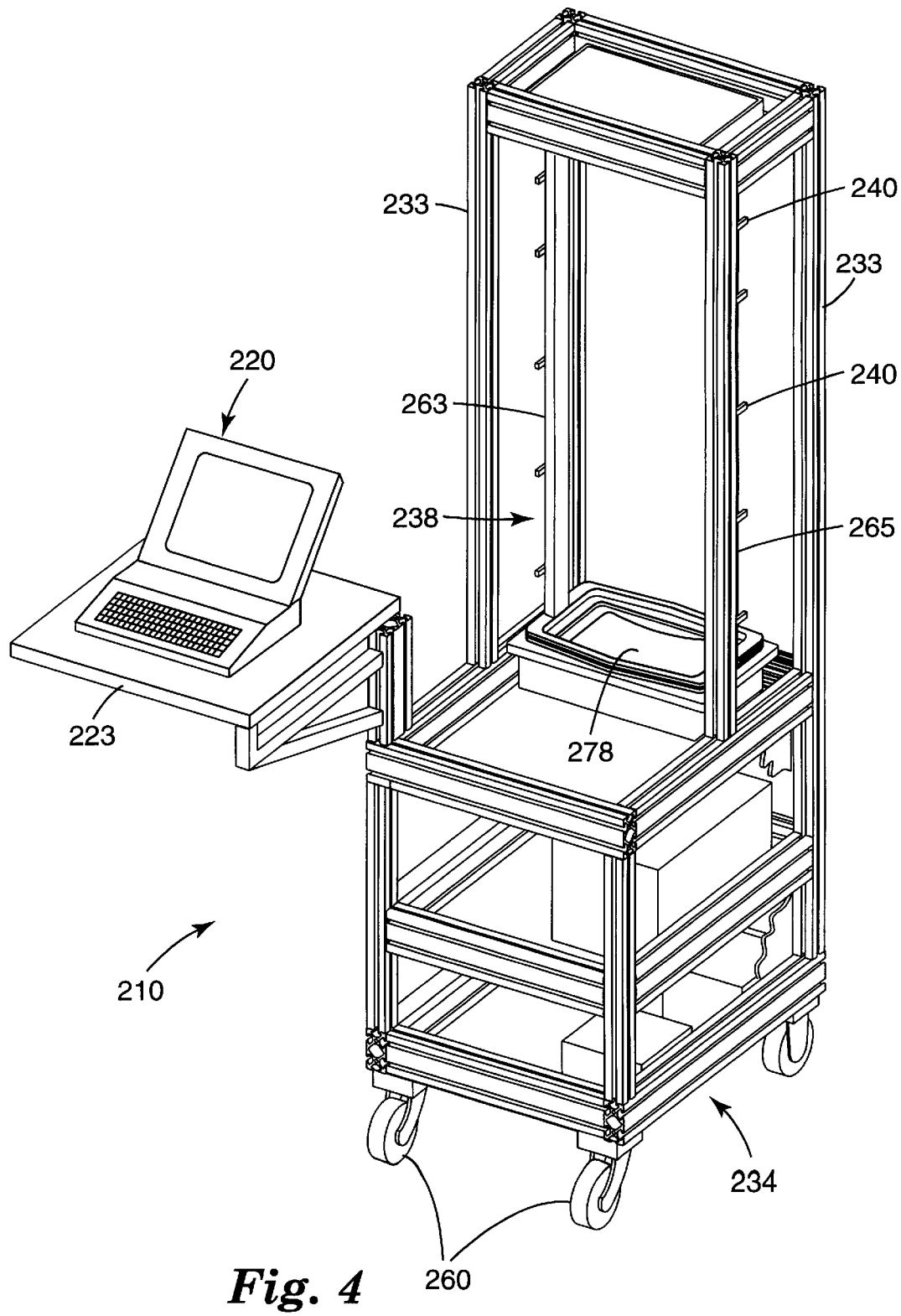
FIG. 4 is a perspective view of the local open-path infrared spectrometry system shown in FIG. 3 with the removable cover removed in accordance with the present invention.

FIG. 3 is a perspective view of one embodiment of the local open-path infrared spectrometry system 210 in accordance with the present invention. In FIG. 3, the spectrometry system 210 shows the removable cover 230 in place such as for calibration of the system 210. FIG. 4 shows a perspective view of a same spectrometry system 210, however, the removable cover 230 is removed from the system 210 to allow a homogenous representative sample of ambient air into the sample path 219. A side view, FIG. 6, of the system 210 is shown with the removable cover 230 in place. The local open-path infrared spectrometry system 210 includes a cart 234 having wheels 260 thereon for providing mobility to the system 210. The cart 234 includes a number of shelves for positioning the necessary spectrometry system components. For example, one shelf is for positioning FTIR spectrometry components 218 such as the infrared source, interferometer, and detector and any other associated elements, such as transfer optics and gas flow control and measurement components as shown in FIG. 1. Another shelf is utilized for positioning of a DC battery source 236 for the unit. Although the unit can be utilized with a DC battery source making it portable, the unit may also be powered with AC.

Further, a shelf 223 is used for positioning of a DC powered laptop computer 220, for portability purposes of the system 210. Otherwise, the laptop computer 220 may be powered by AC. The laptop computer 220 includes the data collection and analysis software for controlling the analysis process and performing quantification of the data collected as previously described and which is well known to those skilled in the art. One example of such software is given in the Example below. However, there are various other software packages suitable for use with spectroscopic systems.

The system 210 further includes an outer frame 232 having four parallel corner members 233. One end of the outer frame 232 is mechanically coupled to the cart 234 and the other end of the outer frame 232 includes an outer frame upper member 235 mechanically connected to the four corner members 233 to form the rectangular shaped outer frame 232.

The outer frame 232 may have mechanical coupling means for positioning a fan or blower to draw air through the outer frame 232 such as to ensure that a homogenous representative sample of ambient air is in the sample path 219 when the air sample data is collected as described with respect to the method in accordance with the present invention.

Inside the outer frame 232 is positioned an inner frame structure 238 to which the removable covers 230 are attached. The removable cover 230 includes a first cover section 252 and a second cover section 254. The inner frame 238 includes an inner frame upper member 239 and inner frame lower member 241. The inner frame 238 also includes an inner frame first side member 263 and an inner frame second side member 265. Each of the inner frame side members 263 and 265 include portions of a fastening means 240 as shown in the detailed diagram of FIG. 5. Such fastening means 240 is utilized for attaching the removable cover sections 252 and 254 to the inner frame 238. Each of the removable cover sections 252 and 254 include other portions of the fastening means for engagement with the fastening means 240 on each of the inner frame side members 263 and 265. The inner frame 238 further includes O-rings 245 and 251 on each inner frame side member 263 and 265 for providing a seal when the removable first and second sections 252 and 254 are positioned on the inner frame 238. The fastening means may be any type of means for attaching the removable cover 230 in position, preferably any latch means capable of exerting locking pressure to produce a sealed sample path when the removable cover is enclosing the sample path. Further, the inner frame 238 includes O-ring 247 about the lower portion of the inner frame upper member 239 and O-ring 246 about the upper portion of inner frame lower member 241 to provide seal with respect to the upper and lower ends of the removable first and second cover sections 252 and 254 when positioned in place to enclose the sample path 219. The removable cover 230 is preferably made of aluminum as are other portions of the enclosure that may have contact with the gas enclosed therein. However, many other materials can be used, such as, for example, Teflon, polyethylene, polypropylene, and other like plastics.

Figure 5:
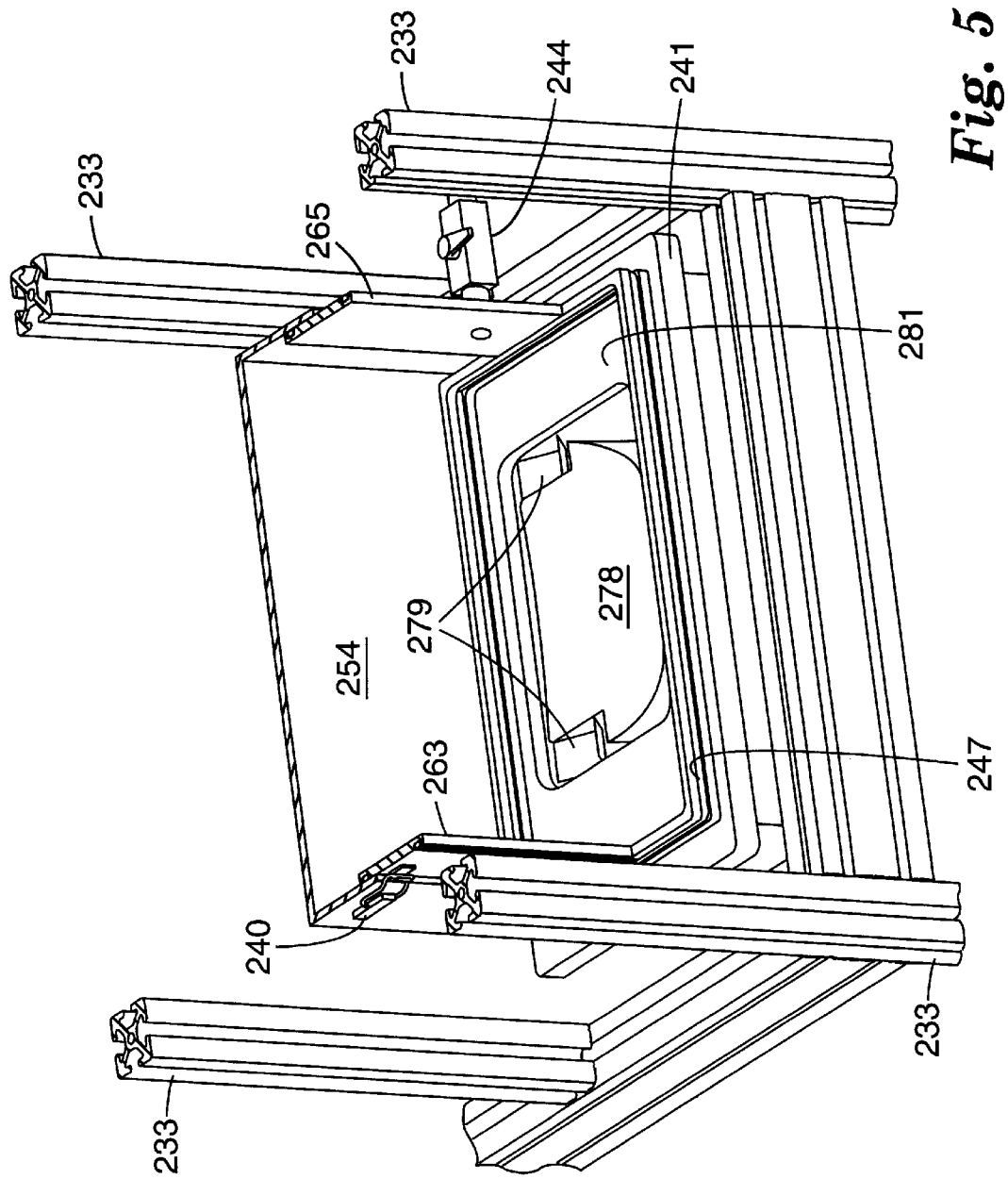
FIG. 5 is a more detailed perspective view taken from the rear of the system shown in FIG. 3 and FIG. 4 with the removable cover partially removed.
Figure 6:
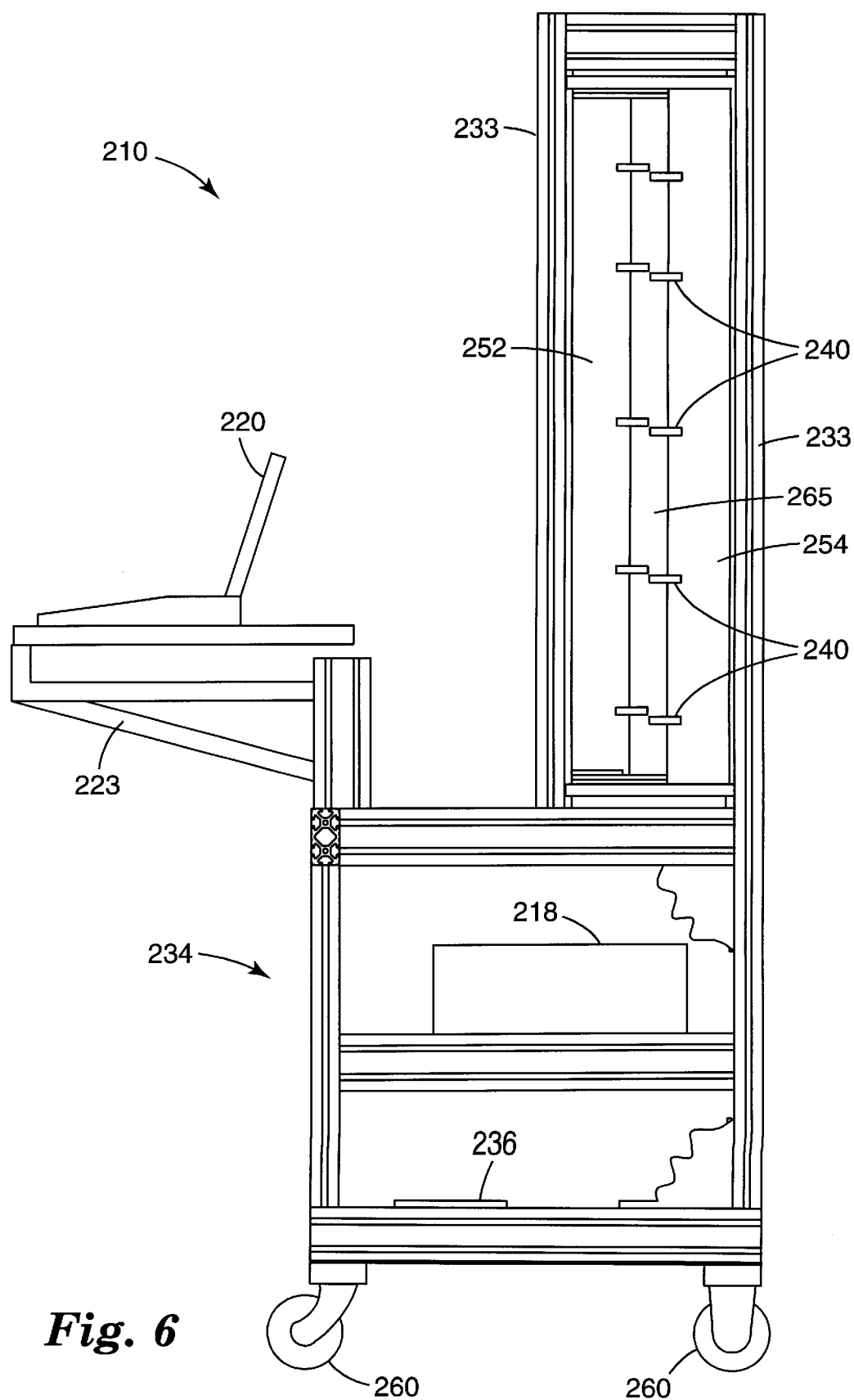
FIG. 6 is a side view of the local open-path infrared spectrometry system shown in FIG. 3 with the removable cover in place.
Figure 9:
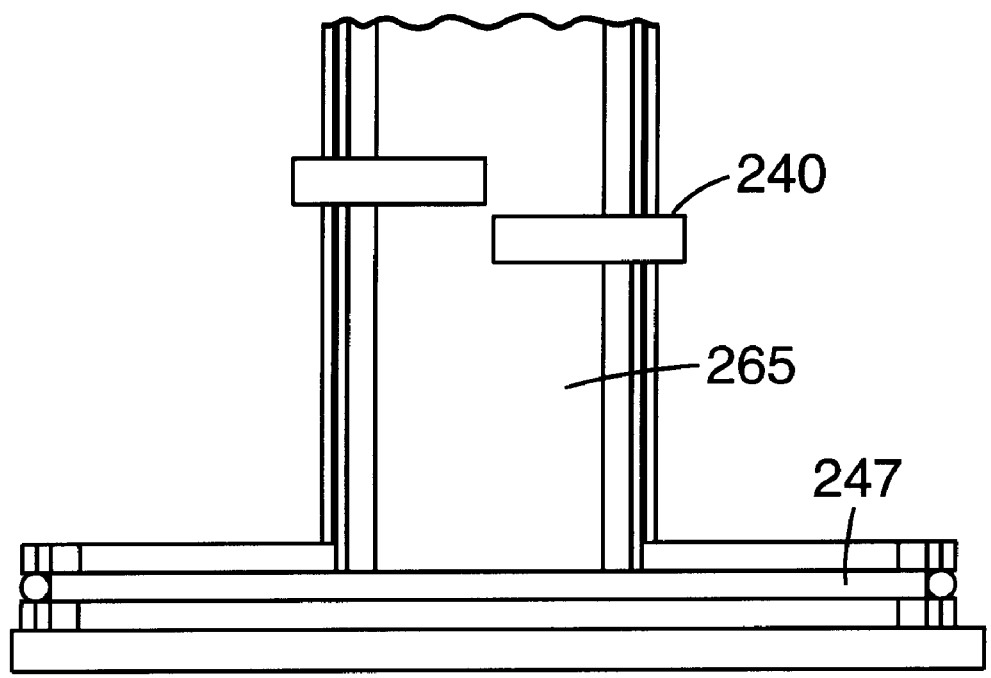
FIG. 9 is a detailed side view of a portion of the frame structure shown in FIG. 7.

As shown in the detail perspective view of FIG. 5, a field mirror 278 is positioned with retroreflective mirrors 279 in the inner frame lower member 241 to form a part of the mirror configuration of the system 210. Not shown are the objective mirrors positioned in the inner frame upper member 239 of the inner frame 238. The mirror configuration may be any known folded path mirror configuration, and is preferably a multi-pass White cell mirror configuration as previously described herein available from Infrared Analysis, Inc., Anaheim, Calif. The mirror 278 is sealed in the opening of platform 281, such as, for example, with use of an O-ring (not shown) under the platform and between the platform 281 and structure mounting the mirror 281. As such, when the removable cover 230 is in place, the sample path is completely sealed and enclosed.

As configured, the mobile local open-path infrared spectrometry system 210 can be operated as an open air spectrometry system when the removable cover 230 is detached using the fastening means 240. This allows a homogenous representative sample of ambient air to enter the sample path 219 defined by the mirror configuration including field mirror 270 and the objective mirrors (not shown). The system 210 would be utilized with the removable cover 230 detached when the ambient air is being sampled in the method described previously with respect to the present invention.

Further, the mobile local open-path infrared spectrometry system 210 may be configured with the removable covers 230 attached as shown in FIG. 3. The removable covers would be positioned about the sample path 219, for example, during at least some of the calibration portions of the method described previously in accordance with the present invention.

The inner frame 238 also includes inlet valve 242 and outlet valve 244 on one of the side members 263 or 265 of the inner frame 238. The inlet and outlet valves 242 and 244 allow for CTS calibration gases to be sampled in a fully enclosed and sealed cell configuration for calibration of the system 210. The gas flow control and measurement components as previously described with reference to FIG. 1 provides the apparatus necessary to perform flushing of the enclosed sample path and injection of various CTS gases or background gases or any other gases utilized in the method that are to be sampled when in an enclosed sample path environment and as attached to the inlet and outlet valves 242 and 244.

Although the system 210 is shown in a vertical state, i.e. the sample path has a length that is perpendicular to the ground, it is recognized that the mirror configuration or any other components of the system 210 may be orientated horizontally and still provide the functionality in accordance with the present invention.

Moreover, although the removable cover includes two removable cover sections 252 and 254, one of skill in the art will recognize that any number of removable covers may be utilized in accordance with the present invention. For example, only one cover may need to be removed with use of a fan drawing or blowing a homogenous representative sample of ambient air into the sample path 219 or one removable cover may be used to enclose the entire sample path. Further, for example, it should be recognized that additional inner frame structure may be utilized such that more than two removable covers are positioned about the sample path. However, by having removable cover sections that can be removed about the entire volume of the sample path typically about 75 liters, but within the range of about 0.5 liters to about 150 liters (i.e., except for the inner frame structure as required in the embodiment of the system 210), a homogenous sample representative of the ambient air is readily available in the sample path without the need for any fan structure.

The following example shows indoor air monitoring results and test procedures for air analysis utilizing an apparatus and method in accordance with the present invention. The purpose of the example is to rapidly assess the levels of 1,1-dichloro-1-fluoroethane (Genesolve) in indoor air at specified locations.

EXAMPLE 1

Figure 10A:
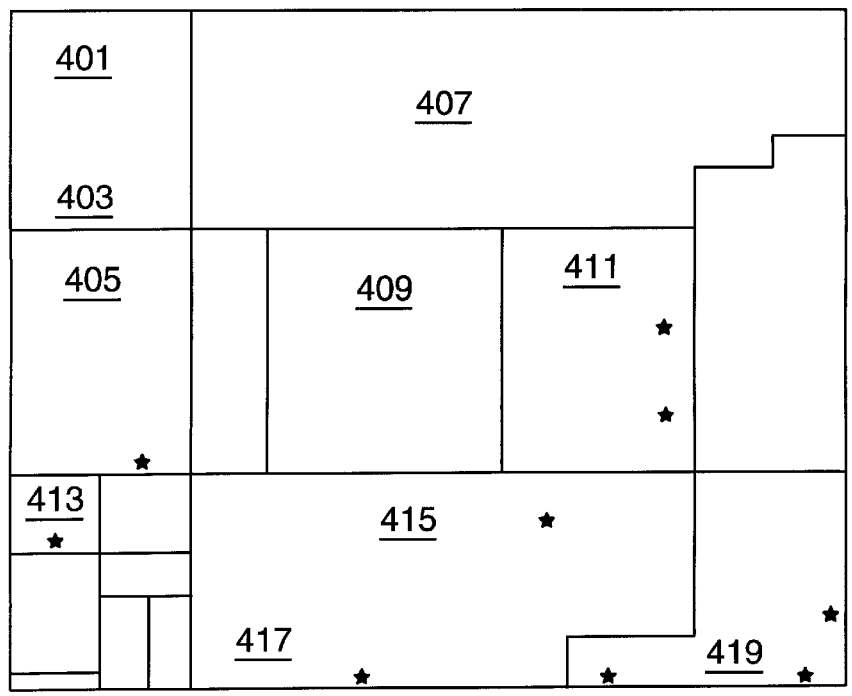
FIG. 10a and FIG. 10b are schematic diagrams of a floor area which is assessed utilizing the local open-path infrared spectrometry system in accordance with the present invention detailed in the Example.
Figure 10B:
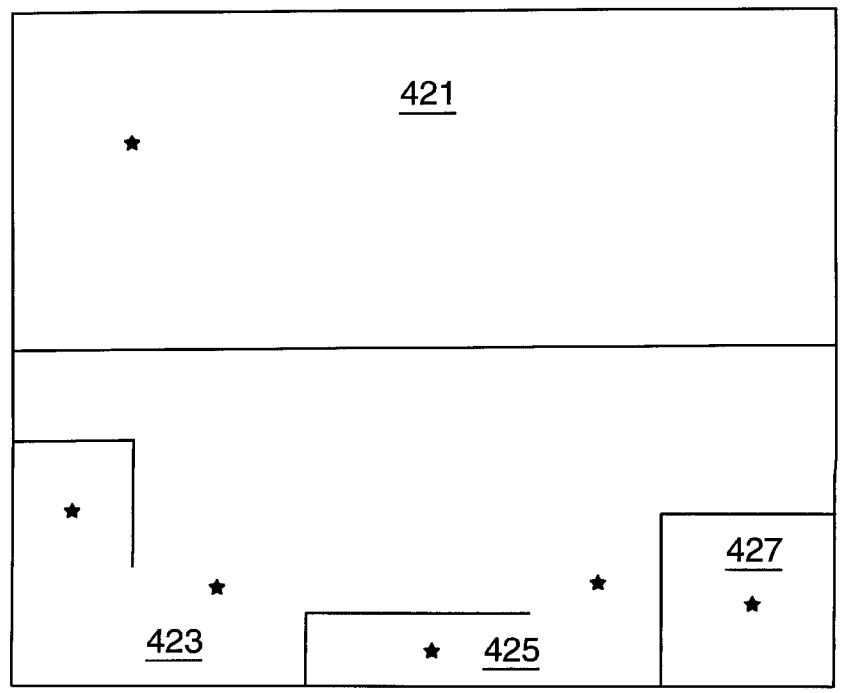

FIGS. 10a and 10b show the facility floor plan of a location where indoor air sampling is performed. All the indoor air sample data is collected in the sample path of a local open-path infrared spectrometry system including the hardware described below, with the sample path being located approximately 3–6 feet above the floor. Table 1 is a summary of the results for the measurement of Genesolve at selected locations throughout the facility. Sixteen separate locations on two floors of the facility are tested in 4.5 hours; each floor including an area of about 31,000 square meters. At least two samples are collected at each location. Genesolve concentrations on the main floor shown in FIG. 10a range from 1.74 ppmv in the office area, to 9.58 ppmv in the rubber molding production area. Genesolve is not detected in the six sampling locations on the basement floor shown in FIG. 10b.

The monitoring protocol generally follows the guidelines outlined in the protocol, U.S. EPA, "Protocol for the Use of Extractive Fourier Transform Infrared (FTIR) Spectrometry for the Analysis of Gaseous Emissions from Stationary Sources," *EMTIC Bulletin Board* (Feb. 3, 1995). The FTIR testing parameters are given further below.

The local open-path infrared spectrometry system utilized is a prototype system constructed, generally in accordance with the overall structural configuration of the system including the removable cover as described with respect to FIGS. 3–9. The spectrometry components include those components of the M2500 available from MIDAC Spectrometer, Irvine, Calif. The multi-pass mirror configuration defining the sample path is a White Cell mirror configuration constructed by Gemini Specialty Optics Inc., Anaheim, Calif. and Infrared Analysis, Inc., Irvine, Calif. The entire system is supplied with power by 12 volt batteries. A 486 laptop computer provides the control/data acquisition and processing functions. The beam splitter of the interferometer is a ZnSe beam splitter and the windows for transfer of the light beam into the sample path are NaCl windows.

The software used with the 486 laptop computer includes several packages. All data collection and analyses is performed using Galactic Software's package "MIDAC Grams/386" (Version 3.01C, Level II, copyrights through 1995). All sample spectra are analyzed using a "Linear Least Squares Fit" (LSF) routine (Rho Squared; Durham, N.C.) operated in "Midac Grams/386." Approximately 10% of all sample spectra are also quantified using computer assisted software subtraction. Calculated uncertainties from the LSF routine are compared to uncertainties determined from the spectral subtraction data reduction technique applied to the same data. It is determined from this comparison that the uncertainties ($\sigma$) from subtraction data reduction are typically three to four times greater than the computer generated uncertainties from LSF calculations. As a result, reported uncertainties from linear least squares fit data reduction are multiplied by four to insure a conservative reported value. The reported uncertainties listed in results Table 1 are $4\sigma$.

The data collected using the local open-path infrared spectrometry system is single beam spectrum data. Boxcar apodization is used. The data collected is at a $0.5\ cm^{-1}$ resolution using 64 co-added scans and a gain=1.

The CTS utilized is a 0.962 ppmv ethylene in balance nitrogen available from Scott Specialty Gases. The background high purity gas is dry nitrogen.

The general test procedure for this example utilizes five steps:

1) Background Spectrum (Sample path—Enclosed)
The enclosed sample path of the local open-path infrared spectrometry system is purged with at least five volumes of high purity dry nitrogen and a single beam spectrum of the high purity dry nitrogen is collected. The nitrogen single beam spectrum is used as the background spectrum for subsequent calibration and analysis of sample data.

2) Water Reference Spectrum (Sample Path—Open & Enclosed)
   a) (Sample Path—Open) The sample path of the local open-path infrared spectrometry system gas cell is opened or in other words the enclosure is removed. A background single beam spectrum of indoor air is collected.
   b) (Sample Path—Enclosed) Using the indoor air background spectrum from step 2)a) above, the local open-path infrared spectrometry system is operated in an active absorbance align mode to match water absorbance. High purity nitrogen is humidified by bubbling through a water impinger and is flushed through the enclosed sample path until water absorbance levels closely matched indoor air levels of water. A single beam spectrum of the humidified nitrogen gas is collected. The single beam spectrum of humidified nitrogen is converted to an absorbance spectrum using the high purity dry nitrogen background spectrum from step 1 above. The absorbance spectrum of the high purity humidified nitrogen is saved as a water reference spectrum and used for spectral subtraction of sample data.

3) Optical Pathlength Calibration (Sample Path—Enclosed)
The optical pathlength of the local open-path infrared spectrometry system is determined quantitatively by the use of a 0.962 ppmv ethylene in balance nitrogen calibration transfer standard (CTS). The enclosed sample path of local open-path infrared spectrometry system is flushed with at least five volumes of the CTS. A single beam spectrum of the CTS is collected. The single beam spectrum of CTS is converted to an absorbance spectrum using the high purity dry nitrogen background spectrum from step 1 above. The CTS absorbance spectrum is quantified using an ethylene reference spectrum to determine the optical pathlength.

4) Indoor Air Sample Data Collection (Sample Path—Open)
The removable cover is removed and indoor air sample data is collected as single beam spectra. Indoor air sample data is collected throughout the facility by sequentially moving the calibrated "on-line" local open-path infrared spectrometry system into the selected sampling areas. The single beam indoor sample data is converted to absorbance spectra using the high purity dry nitrogen background spectrum from 1 above. The sample absorbance spectra are quantified using a Genesolve reference spectrum to determine facility indoor levels of Genesolve as ppmv.

5) Final Instrument and Optical Pathlength Calibration (Sample Path—Enclosed)
The optical pathlength is determined quantitatively by the use of a 0.962 ppmv ethylene in balance nitrogen CTS. The enclosed sample path is flushed with at least five volumes of the CTS. A single beam spectrum of the CTS is collected. The single beam spectrum of CTS is converted to an absorbance spectrum using the high purity dry nitrogen background spectrum from step 1 above. The CTS absorbance spectrum is quantified using the CTS absorbance spectrum generated from step 3 above to determine the instrument and optical pathlength stability from the initiation through completion of sample generation.

TABLE 1

| Sample Location | Sample | Time | Genesolve (ppmv) | Uncertainty (ppmv) |
|---|---|---|---|---|
| Main Floor | | | | |
| Liquid Resins | A1 | 13:26 | 4.33 | 0.12 |
| Liquid Resins | A2 | 13:29 | 5.65 | 0.16 |
| Liquid Resins | A3 | 13:33 | 6.58 | 0.20 |
| Liquid Resins | B1 | 13:38 | 6.83 | 0.20 |
| Liquid Resins | B2 | 13:41 | 6.67 | 0.20 |
| Spring Winding | C1 | 13:49 | 4.94 | 0.16 |
| Spring Winding | C2 | 13:53 | 4.82 | 0.16 |
| Electrical Terminations | D1 | 13:59 | 7.52 | 0.24 |
| Electrical Terminations | D2 | 14:03 | 7.43 | 0.24 |
| Core Winding | E1 | 14:10 | 7.03 | 0.24 |
| Core Winding | E2 | 14:14 | 6.45 | 0.20 |
| Office Area | F1 | 14:30 | 1.74 | 0.08 |
| Office Area | F2 | 14:34 | 1.98 | 0.08 |
| Office Area | G1 | 14:38 | 3.38 | 0.12 |
| Office Area | G2 | 14:40 | 3.44 | 0.12 |

TABLE 1-continued

| Sample Location | Sample | Time | Genesolve (ppmv) | Uncertainty (ppmv) |
|---|---|---|---|---|
| Office Area | H1 | 14:46 | 3.42 | 0.12 |
| Office Area | H2 | 14:49 | 3.75 | 0.12 |
| Rubber Molding | I1 | 14:56 | 8.69 | 0.72 |
| Rubber Molding | I2 | 15:00 | 9.58 | 0.96 |
| Rubber Molding | J1 | 15:03 | 1.65 | 0.12 |
| Rubber Molding | J2 | 15:06 | 4.29 | 0.20 |
| Rubber Molding Basement Floor | J3 | 15:08 | 2.16 | 0.12 |
| Warehouse | K1 | 15:20 | ND | 0.04 |
| Warehouse | K2 | 15:28 | ND | 0.04 |
| Warehouse | L1 | 15:34 | ND | 0.04 |
| Cable Process | M1 | 15:39 | ND | 0.04 |
| Cable Process | M2 | 15:43 | ND | 0.04 |
| Elevator | N1 | 15:47 | ND | 0.04 |
| Stairwell | O1 | 15:51 | ND | 0.04 |
| By Elevator | P1 | 15:57 | ND | 0.04 |
| By Elevator | P2 | 16:01 | ND | 0.04 |

Although the invention has been described with particular reference to preferred embodiments thereof, variations and modifications of the present invention can be made within a contemplated scope of the following claims as is readily known to one skilled in the art.

What is claimed is:

1. An open air analysis apparatus, comprising:
    an optical source for providing an optical signal;
    an interferometer for modulating the optical signal;
    an optical signal detector; and
    a sample cell, comprising a folded path mirror configuration defining a sample path through which the optical signal passes from said interferometer to said optical signal detector, a housing disposed longitudinally about the sample path, and first and second end caps disposed on opposing ends of said housing;
wherein said housing has at least one removable portion for allowing entry into said sample path of a sample of ambient air when said at least one removable portion is removed and wherein said apparatus is for open air analysis.

2. The apparatus of claim 1, wherein said optical source is an infrared source.

3. The apparatus of claim 1, wherein said folded path mirror configuration is a White cell folded path mirror configuration.

4. The apparatus of claim 1, wherein said sample cell further comprises a sample inlet port and a sample outlet port.

5. The apparatus of claim 1, wherein said housing includes at least a first and second removable portion.

6. The apparatus of claim 5, wherein said sample cell further comprises support means for supporting said folded path mirror configuration between said endcaps, and wherein said first and second removable portions are positioned about said sample path such that when said first and second removable portions are removed, air moves into said sample path from substantially all directions between said first and second endcaps.

7. The apparatus of claim 6, wherein said sample cell further comprises at least one member extending between said first and second endcaps to which said first and second removable portions are attached and sealed.

8. The apparatus of claim 7, wherein said endcaps comprise a sample inlet port and a sample outlet port.

9. The apparatus of claim 1, further comprising means for moving the representative sample of ambient air into said sample path when said at least one removable portion is removed.

10. The apparatus of claim 1, wherein the combination is configured as a movable standalone open air analysis apparatus powered by a battery source.

11. The apparatus of claim 10, wherein the movable standalone analysis apparatus includes a processing device for receiving data signals from the optical signal detector.

12. The apparatus of claim 1, wherein said sample cell further comprises a frame structure having a first and second ends for supporting the folded path mirror configuration therebetween, and further wherein said at least one removable portion includes first and second removable portions positioned within said frame structure about the sample path such that when said first and second removable portions are removed, air moves into said sample path from substantially all directions between said first and second ends, and wherein said frame structure is mounted vertically with respect to the ground on a movable platform.

13. A device for an optical analysis system, comprising:
    a folded path mirror configuration defining a sample path through which an optical signal is passed; and
    an enclosure for enclosing and sealing the sample path, the enclosure comprising (a) a housing disposed longitudinally about said sample path, said housing terminating in first and second openings and including at least one removable portion for allowing entry into the sample path of a representative sample of ambient air when the at least one removable portion is removed; and (b) first and second terminal portions disposed over said first and second openings of said housing.

14. The device of claim 13, wherein said folded path mirror configuration is a White cell folded path mirror configuration.

15. The device of claim 13, wherein said enclosure further comprises a sample inlet port and a sample outlet port.

16. The device of claim 13, wherein said enclosure has at least a first and second removable portion.

17. The device of claim 16, wherein said enclosure further comprises a frame structure having a first and second ends for supporting said folded path mirror configuration therebetween, and wherein said first and second removable portions are positioned within said frame structure about said sample path such that when said first and second removable portions are removed, air moves into said sample path from substantially all directions between said first and second ends.

18. The device of claim 17, wherein said enclosure further includes at least one member extending between said first and second ends to which said first and second removable portions are attached and sealed.

19. The device of claim 18, wherein said at least one member includes a sample inlet port and a sample outlet port.

20. A method of gas analysis, comprising the steps of:
    providing an open air spectrometry system defining a sample path;
    enclosing and sealing the sample path;
    calibrating the open air spectrometry system with the sample path enclosed and sealed;
    opening the sample path to allow ambient air therein; and
    initiating analysis of a sample of ambient air in the sample path.

21. The method according to claim 20, further including the steps of:
    enclosing and sealing the sample path after analysis of the sample of ambient air; and
    recalibrating the open air spectrometry system to determine the stability of the system during ambient air sample analysis.

22. The method according to claim 20, wherein the calibrating step includes the steps of:
introducing a calibration transfer standard into the enclosed and sealed sample path;
determining an optical pathlength of the defined sample path using the calibration transfer standard in the enclosed and sealed sample path; and
removing the calibration transfer standard from the enclosed and sealed sample path.

23. The method according to claim 22, wherein the calibrating step further includes generating background spectrum data for a high purity dry gas and spectrum data for a high purity humidified gas prior to or after the introducing step.

24. The method according to claim 23, wherein the optical pathlength determining step includes the steps of:
collecting spectrum data for the calibration transfer standard;
converting the spectrum data for the calibration transfer standard to absorbance spectrum data using the background spectrum data for the high purity dry gas; and
quantifying the absorbance spectrum for the calibration transfer standard using a calibration transfer standard reference spectrum.

25. The method according to claim 24, wherein the analysis initiation step includes the steps of:
collecting spectrum data representative of the ambient air sample;
converting the spectrum data representative of the ambient air sample to absorbance spectrum data for the ambient air sample using the background spectrum data for the high purity dry gas; and
quantifying the absorbance spectrum data for the ambient air sample using at least one particular gas reference spectrum.

26. The method according to claim 22, wherein the calibrating step further includes the following steps prior to or after the introducing step:
introducing a high purity gas into the enclosed and sealed path;
collecting background spectrum data for the high purity gas;
opening the sample path to allow ambient air therein;
collecting ambient air background spectrum data for the ambient air;
enclosing and sealing the sample path;
introducing a humidified high purity gas into the enclosed and sealed path until water absorbance levels of the humidified high purity gas match the water absorbance levels of the ambient air background spectrum data;
collecting spectrum data for the humidified high purity gas; and
converting the spectrum data for the humidified high purity gas to an absorbance spectrum using the background spectrum data for the high purity gas.

27. The method according to claim 20, wherein the initiating step includes the step of starting an air movement device to introduce a representative sample of ambient air into the sample path.

28. The method according to claim 20, wherein the method further includes the step of locating the open air spectrometry system in a first environment and wherein the method further includes the step of moving the open air spectrometry system to a second environment.

29. The method according to claim 20, wherein the providing step includes providing an open air spectrometry system including a folded path mirror configuration, the open air spectrometry system having a calibrated state and an uncalibrated state, and further wherein the enclosing and sealing the sample path step includes the step of providing an enclosure including at least one removable portion to provide the sample path with the ambient air while maintaining the calibrated state when the at least one removable cover is removed.

30. The method according to claim 29, wherein the enclosure includes at least a first and second removable portion.

31. The method according to claim 30, wherein the enclosure includes a frame structure having a first and second end for supporting the folded path mirror configuration therebetween, and further wherein the first and second removable portions are positioned within the frame structure about the sample path such that when the first and second removable portions are removed, air moves into the sample path from substantially all directions between the first and second ends.

* * * * *

UNITED STATES PATENT AND TRADEMARK OFFICE
CERTIFICATE OF CORRECTION

PATENT NO. : 6,134,004
DATED : October 17, 2000
INVENTOR(S) : William K. Reagen et al.

Page 1 of 1

It is certified that error appears in the above-identified patent and that said Letters Patent is hereby corrected as shown below:

Title page,
Under the subheading of "U.S. PATENT DOCUMENTS" under "References Cited" please insert:
-- 3,860,818    1/1975      Stalder et al.
   5,068,798    11/1991     Heath et al. --.
Under the subheading of "FOREIGN PATENT DOCUMENTS" under "References Cited" please insert:
-- 0 006 749    1/1980      (EP)
   2 190 184    11/1987     (UK)
   2,281,967    3/1995      (UK) --.

Column 16,
Line 8, please delete the article "a", second instance.
Line 36, please delete the article "a", second instance.

Signed and Sealed this

Eighteenth Day of December, 2001

Attest:

JAMES E. ROGAN
*Attesting Officer*    *Director of the United States Patent and Trademark Office*